(12) United States Patent
Grbic et al.

(10) Patent No.: US 9,155,470 B2
(45) Date of Patent: Oct. 13, 2015

(54) METHOD AND SYSTEM FOR MODEL BASED FUSION ON PRE-OPERATIVE COMPUTED TOMOGRAPHY AND INTRA-OPERATIVE FLUOROSCOPY USING TRANSESOPHAGEAL ECHOCARDIOGRAPHY

(71) Applicants: Reinhard Boese, Wuerzburg (DE)
Ursula Boese, Wuerzburg (DE) Antje Schulte, Eckental (DE)

(72) Inventors: Sasa Grbic, Princeton, NJ (US); Peter Mountney, London (GB); Razvan Ioan Ionasec, Nuremberg (DE); Matthias John, Nuremberg (DE); Jan Boese, Eckental (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 217 days.

(21) Appl. No.: 13/741,610

(22) Filed: Jan. 15, 2013

(65) Prior Publication Data
US 2013/0279780 A1     Oct. 24, 2013

Related U.S. Application Data

(60) Provisional application No. 61/589,961, filed on Jan. 24, 2012.

(51) Int. Cl.
*A61B 5/02*      (2006.01)
*A61B 6/00*      (2006.01)
(Continued)

(52) U.S. Cl.
CPC ............... *A61B 5/0033* (2013.01); *A61B 6/12* (2013.01); *A61B 6/487* (2013.01); *A61B 6/5247* (2013.01);
(Continued)

(58) Field of Classification Search
CPC ... G06T 7/0012; G06T 7/0024; G06T 7/0028; G06T 2207/10072; G06T 2207/10121; G06T 2207/10124; G06T 2207/10132; G06T 2207/30021; G06T 2207/30048; A61B 5/0421; A61B 5/061; A61B 5/066; A61B 6/5229; A61B 6/5235; A61B 6/5247; A61B 8/5261
USPC .................................. 382/128, 131, 132, 294
See application file for complete search history.

(56) References Cited

U.S. PATENT DOCUMENTS 7,327,872 B2 *   2/2008   Vaillant et al. ................ 382/154
7,916,919 B2     3/2011   Zheng et al.
(Continued)

OTHER PUBLICATIONS

Gao et al., "Rapid Image Registration of Three-Dimensional Transesophageal Echocardiography and X-ray Fluoroscopy for the Guidance of Cardiac Interventions", In Proceedings of the First International Conference on Information Processing in Computer-Assisted Interventions, 2010, pp. 124-134.
(Continued)

*Primary Examiner* — Michael A Newman (57) ABSTRACT

A method and system for model-based fusion of pre-operative image data and intra-operative fluoroscopic images is disclosed. A fluoroscopic image and an ultrasound image are received. The ultrasound image is mapped to a 3D coordinate system of a fluoroscopic image acquisition device used to acquire the fluoroscopic image. Contours of an anatomical structure are detected in the ultrasound image, and a transformation is calculated between the ultrasound image and a pre-operative CT image based on the contours and a patient-specific physiological model extracted from the pre-operative CT image. A final mapping is determined between the CT image and the fluoroscopic image based on the transformation between the ultrasound image and physiological model and the mapping of the ultrasound image to the 3D coordinate system of the fluoroscopic image acquisition device. The CT image or the physiological model can then be projected into the fluoroscopic image.

29 Claims, 7 Drawing Sheets

(51) Int. Cl.

| | | |
|---|---|---|
| *A61B 8/13* | (2006.01) | |
| *A61B 8/00* | (2006.01) | |
| *G06T 7/00* | (2006.01) | |
| *G06T 5/50* | (2006.01) | |
| *A61B 5/00* | (2006.01) | |
| *A61B 8/08* | (2006.01) | |
| *A61B 8/12* | (2006.01) | |
| *A61B 6/12* | (2006.01) | |

(52) U.S. Cl.
CPC ............ *A61B 6/5264* (2013.01); *A61B 8/0883* (2013.01); *A61B 8/12* (2013.01); *A61B 8/4245* (2013.01); *A61B 8/466* (2013.01); *A61B 8/5261* (2013.01); *A61B 8/5276* (2013.01); *G06T 5/50* (2013.01); *G06T 7/0038* (2013.01); *G06T 7/0042* (2013.01); *G06T 2207/10016* (2013.01); *G06T 2207/10081* (2013.01); *G06T 2207/10121* (2013.01); *G06T 2207/10132* (2013.01); *G06T 2207/20072* (2013.01); *G06T 2207/20076* (2013.01); *G06T 2207/20081* (2013.01); *G06T 2207/20221* (2013.01)

(56) References Cited

U.S. PATENT DOCUMENTS

| | | | |
|---|---|---|---|
| 8,116,548 B2 | 2/2012 | Zheng et al. | |
| 2005/0197559 A1* | 9/2005 | Boese et al. | 600/407 |
| 2007/0167706 A1* | 7/2007 | Boese et al. | 600/407 |
| 2008/0095421 A1* | 4/2008 | Sun et al. | 382/131 |
| 2008/0283771 A1* | 11/2008 | Li | 250/459.1 |
| 2008/0287805 A1* | 11/2008 | Li | 600/471 |
| 2009/0105579 A1* | 4/2009 | Garibaldi | 600/409 |
| 2010/0239144 A1* | 9/2010 | Fichtinger et al. | 382/131 |
| 2010/0254583 A1 | 10/2010 | Chan et al. | |
| 2010/0290685 A1* | 11/2010 | Wein et al. | 382/131 |
| 2011/0060576 A1 | 3/2011 | Sharma et al. | |
| 2012/0022843 A1 | 1/2012 | Ionasec et al. | |
| 2012/0059249 A1* | 3/2012 | Verard et al. | 600/424 |
| 2012/0059253 A1 | 3/2012 | Wang et al. | |
| 2012/0296202 A1 | 11/2012 | Mountney et al. | |

OTHER PUBLICATIONS

Gao et al., "Registration of 3D Trans-esophageal Echocardiography to X-ray Fluoroscopy Using Image-Based Probe Tracking," Medical Image Analysis, 2011.

Ionasec et al., "Robust Motion Estimation Using Trajectory Spectrum Learning: Application to Aortic and Mitral Valve Modeling from 4D TEE", Proceedings of 12th IEEE International Conference on Computer Vision, 2008, pp. 1601-1608, the disclosures of which are incorporated herein by reference.

Ionasec et al., "Patient-Specific Modeling and Quantification of the Aortic and Mitral Valves from 4D Cardiac CT and TEE", IEEE Transactions on Medical Imaging, 2010, 17 pp.

Lang et al., "US—Fluoroscopy Registration for Transcather Aortic Valve Implantation", IEEE Trans. Biomed. Eng., May 2012; 59(5): 1444-53; Epub Feb. 28, 2012, 10 pp.

L. Shapira et al., "contextual Part Analogies in 3D Objects", International Journal of Computer Vision, 2010, pp. 89: 309-326.

* cited by examiner

METHOD AND SYSTEM FOR MODEL BASED FUSION ON PRE-OPERATIVE COMPUTED TOMOGRAPHY AND INTRA-OPERATIVE FLUOROSCOPY USING TRANSESOPHAGEAL ECHOCARDIOGRAPHY

This application claims the benefit of U.S. Provisional Application No. 61/589,961, filed Jan. 24, 2012, the disclosure of which is herein incorporated by reference.

BACKGROUND OF THE INVENTION

The present invention relates to the fusion of multi-modal medical images, and more particularly, to model based fusion of pre-operative computed tomography (CT) and intra-operative fluoroscopic images using Transesophageal Echocardiography (TEE).

In current clinical practice, minimally invasive percutaneous cardiac interventions, such as Transcatheter Aortic Valve Implantation (TAVI), are becoming more prevalent as compared with traditional open heart surgical procedures. Such minimally invasive percutaneous cardiac interventions have advantages of shorter patient recovery times, as well as faster and less risky procedures that d not require anesthesia. In such minimally invasive cardiac interventions, devices such as implants are delivered into the patient through vessels via a catheter. Navigating the catheter inside the vessels of a patient is challenging. X-ray fluoroscopy is typically used to visualize the catheter; however, this imaging modality does not capture soft tissue structure of the patient well. A contrast medium can be injected periodically through the catheter to enhance the fluoroscopy image and enable the view of the vessel and surrounding tissue. In addition, a second imaging modality, such as Transesophageal Echocardiography (TEE), is often used in the operating room in order to visualize soft tissue. However, TEE has a small field of view and thus can only display a limited context of the soft tissue.

Visualization of the catheter and the surrounding soft tissue typically requires two display in the operating room, one showing the TEE and the other showing the fluoroscopy image. The surgeon must interpret the two separately displayed imaging modalities, extract relevant information, and spatially transform the information between the two coordinate systems and ultimately into the patient.

BRIEF SUMMARY OF THE INVENTION

The present invention provides a method and system for fusion of pre-operative image data, such as pre-operative computed tomography (CT), and intra-operative fluoroscopic images using Transesophageal Echocardiography (TEE). The fusion of CT, fluoroscopy, and ultrasound into a single visualization has the potential to simply navigation in transcatheter intervention procedures. Embodiments of the present invention enable patient-specific physiological models extracted from pre-operative data, such as cardiac CT, to be visualized in the fluoroscopic workspace. Embodiments of the present invention bring dynamic motion compensated patient-specific models from pre-operative CT to intra-operative fluoroscopic images by using TEE as an intermediate modality.

In one embodiment of the present invention, a 2D location of an ultrasound probe is detected in a fluoroscopic image acquired using a fluoroscopic image acquisition device. A 3D pose of the ultrasound probe is estimated based on the detected 2D location of the ultrasound probe in the fluoroscopic image. An ultrasound image is mapped to a 3D coordinate system of the fluoroscopic image acquisition device based on the estimated 3D pose of the ultrasound probe. Contours of an anatomical structure are detected in the ultrasound image. A transformation is calculated between the ultrasound image and a pre-operative CT image based on the contours detected in the ultrasound image and a patient-specific physiological model extracted from the pre-operative CT image. A final mapping is determined between the pre-operative CT image and the fluoroscopic image based on the transformation between the ultrasound image and the patient-specific physiological model extracted from the pre-operative CT image and the mapping of the ultrasound image to the 3D coordinate system of the fluoroscopic image acquisition device.

These and other advantages of the invention will be apparent to those of ordinary skill in the art by reference to the following detailed description and the accompanying drawings.

DETAILED DESCRIPTION

The present invention relates to fusion of pre-operative image data, such as pre-operative computed tomography (CT) with intra-operative fluoroscopic images using Transesophageal Echocardiography (TEE). Embodiments of the present invention are described herein to give a visual understanding of the model-based image fusion method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a method of fusing pre-operative CT and x-ray fluoroscopy images using ultrasound (TEE) images. In various embodiments of the present invention, a complex patient-specific model of cardiac structures is extracted from pre-operative CT, and using contour features extracted from TEE, a mapping to the fluoroscopy coordinate system is determined. Embodiments of the present invention first detect an orientation and position of the ultrasound probe (used to acquire TEE images) in a fluoroscopic image. As the orientation of the TEE fan and the probe are fixed in the fluoroscopy, contours of an intermediate anatomy, such as the mitral valve or the aortic valve, are detected from either 2D ultrasound, X-plane TEE with two orthogonal 2D TEE images, or 3D TEE directly. The contours of the intermediate anatomy are then mapped to the full 3D (or 4D) model of the cardiac structures extracted from the pre-operative CT. The model of the cardiac structures can then be mapped back to the fluoroscopic image from the pre-operative CT using the intermediate TEE ultrasound.

Embodiments of the present invention enable visualization of high-quality pre-operative CT images in fluoroscopy to provide guidance during intervention procedures. By fusing physiological models from pre-operative CT with intra-operative fluoroscopic images, embodiments of the present invention provide visualization of patient-specific physiological models with a large spatial context in the fluoroscopic workspace, as apposed to the limited spatial context of models extracted from TEE images. By using contour features extracted from TEE to fuse the patient-specific models and pre-operative CT images with the fluoroscopic images, the models and pre-operative CT images are breathing motion compensated when displayed in the fluoroscopy and the models and pre-operative CT images fused with the fluoroscopy are updated in real-time. Embodiments of the present invention can be used to incorporate multi-phase CT comprehensive dynamic patient-specific models into the operating room. Embodiments of the present invention are completely image-based, and there is no need for costly magnetic or optical trackers for the ultrasound probe.

Figure 1:
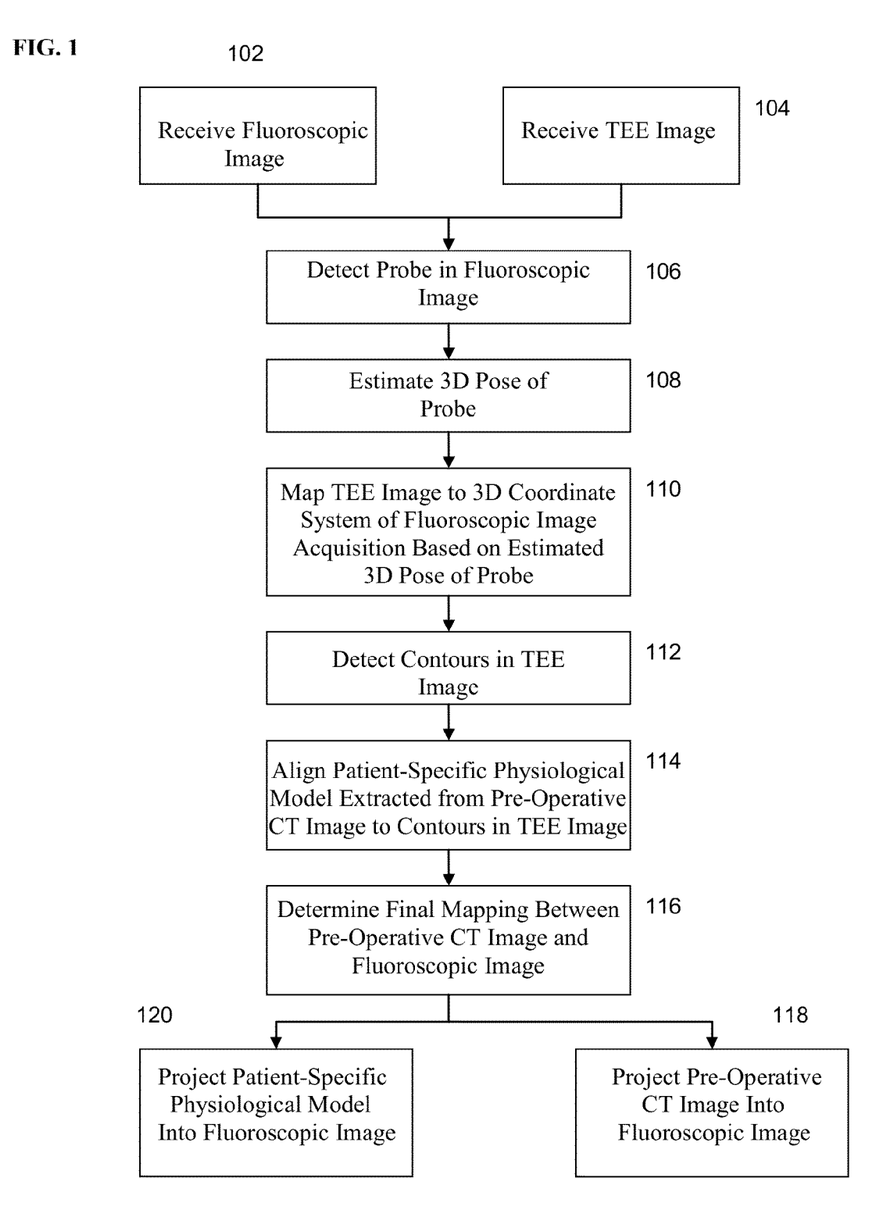
FIG. 1 illustrates a method for model-based fusion of pre-operative CT and intra-operative fluoroscopic images using Transesophageal Echocardiography (TEE) ultrasound, according to an embodiment of the present invention.
Figure 2:
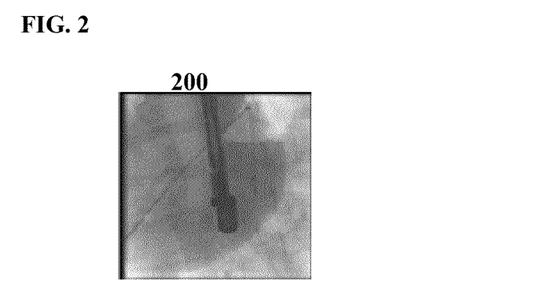
FIG. 2 illustrates an exemplary fluoroscopic image.

FIG. 1 illustrates a method for model-based fusion of pre-operative CT and intra-operative fluoroscopic images using TEE, according to an embodiment of the present invention. At step 102, a fluoroscopic image is received. The fluoroscopic image is a 2D x-ray image and can be received directly from an image acquisition device, such as a C-arm image acquisition device. It is to be understood that the fluoroscopic image may be one of a sequence of fluoroscopic images and may be received in real-time during a cardiac intervention procedure. FIG. 2 illustrates an exemplary fluoroscopic image 200.

Returning to FIG. 1, at step 104, a TEE image is received. The TEE image is an ultrasound image that is acquired using a probe with an ultrasound transducer at the tip that is passed into a patient's esophagus. The TEE image may be received directly from the probe in real-time during the cardiac intervention procedure. In an advantageous implementation, the TEE image may be acquired at the same time as the fluoroscopic image received in step 102.

At step 106, the probe is detected in the fluoroscopic image. The probe detection identifies the location of the probe head used in the fluoroscopic image. The probe head is rigid and can move in 3D space with six degrees of freedom (DOF). The probe's location in the fluoroscopic image is defined by two parameters, i.e., the x and y position in the image space. The probe has the potential to move in six DOF and therefore the detection should be robust to changes in scale, translation, and rotation. In clinical practice, the probe's movement is restricted by anatomy and operating room configuration. This prior knowledge can be used to improve detection of the probe's location in the fluoroscopic image.

According to an advantageous implementation, a learning based method can be used for probe detection. Learning based methods are robust to noise and capable of handling large variations in appearance. Unlike matching or similarity measures, learning based methods are trained on a set of manually annotated or synthetically generated training data. In particular, a probe detector is trained using a learning based method offline prior to receiving the fluoroscopic image, and the trained probe detector is used to detect an image patch in the fluoroscopic image that contains the ultrasound probe head. In order to train a probe detector, synthetic data can be generated by using a computed tomography (CT) volume of an ultrasound probe. DRR images are generated from the CT volume of the probe in a variety of known poses. Manually annotated training data is also chosen to contain a wide variety of pose orientations and locations in various fluoroscopic images. Additionally, the training data set can include images without a probe to enable to trained probe detector to correctly classify non-object regions. The training method is generic and independent of the probe type. The training data is probe specific and is performed offline prior to online detection.

In a possible implementation, a probabilistic boosting tree (PBT) can be used to train the probe detector from the training data. The PBT can be trained using Haar features extracted image patches in the training data annotated as positive (belonging to the probe) or negative (belonging to tissue other than the probe). At runtime, in order to detect the probe in the received fluoroscopic image, Haar features are extracted from image patches in the fluoroscopic image and the trained PBT classifier determines a probability score for each image patch. The image patch having the highest probability score is determined to be the position of the probe in the fluoroscopic image.

Figure 3:
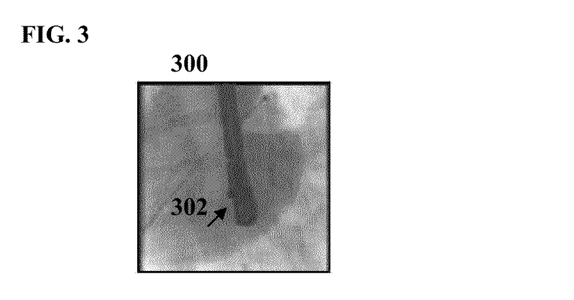
FIG. 3 illustrates probe detection in a fluoroscopic image.

Once the probe is detected in the first frame, a filter, such as an extended Kalman filter or a particle filter, may be used to predict a position of the probe in the next frame. This predicted position can be used to generate a reduced search space. Accordingly, if the fluoroscopic image received at step 102 is a subsequent frame in a sequence of fluoroscopic images, a reduced search space can be determined in the fluoroscopic image based on the probe detection results in the previous frame. In this case, the trained probe detector evaluates only image patches in the reduce search space to detect the probe location. The detected probe location is then used to update the filter state to account for noise in the measurement. FIG. 3 illustrates probe detection in a fluoroscopic image. As shown in FIG. 3, an ultrasound probe 302 is detected in a fluoroscopic image 300 using a trained probe detector.

Returning to FIG. 1, at step 108, a pose of the probe in 3D is estimated. In particular, the pose of the probe relative to the fluoroscopic image is defined by defining the probe's position in 3D (X, Y, Z) and its orientation (roll, pitch, yaw) in the coordinate system of the x-ray fluoroscopic image (i.e., the coordinate system of the C-arm image acquisition device). The detected position of the probe in the 2D fluoroscopic image can be used as a starting point for probe pose estimation using a marginal space learning (MSL) framework.

Figure 4:
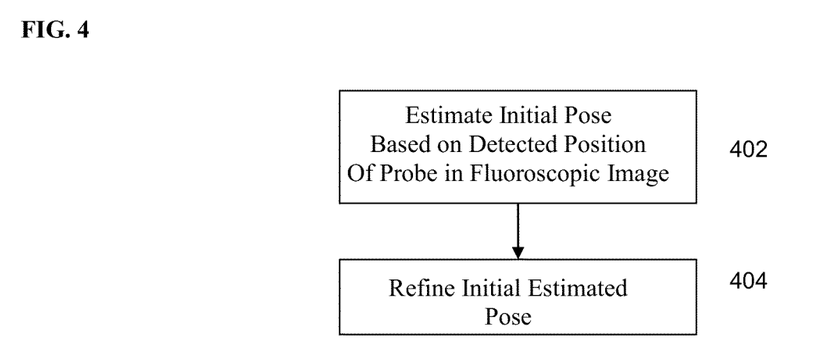
FIG. 4 illustrates a method for estimating the pose according to an embodiment of the present invention.

FIG. 4 illustrates a method for estimating the pose according to an embodiment of the present invention. The method of FIG. 4 can be used to implement step 108 of FIG. 1. As illustrated in FIG. 4, at step 402, an initial pose of the probe is estimated based on the detected position of the probe in the fluoroscopic image. In order to estimate the initial pose of the probe, a marginal space learning approach can be used such that the pose is not estimated directly in the full similarity transformation space, but incrementally on projected sample distributions. This enables fast and directed computation. The 2D position of the probe from the probe detection step is used to initialize pose estimation by estimating the X and Y coordinates of the probe. In order to estimate the pose of the probe in 3D, the 3D position (X, Y, Z) of the probe is estimated in a first detection stage, followed by estimation of the position and orientation in a second detection stage.

Learning based techniques are used for each detection stage. This approach treats pose estimation as a classification problem. A training dataset of the probe in different poses is generated offline. The training set can include manually annotated and synthetically generated training data. In a possible implementation, separate PBT classifiers are trained for each detection stage (i.e., position and position-orientation) of the pose estimation. At run time, features (e.g., Haar features) are extracted from the fluoroscopic image and used by the sequence of trained classifiers to estimate the pose of the probe. This approach is fast and provides an initial estimate of the probe's position and orientation.

Similar to as described above in the probe detection step, a filter, such as an extended Kalman filter or a particle filter, can be used to exploit temporal information between the frames. This reduces the search space, enabling the pose of the probe to be predicted in subsequent frames of a fluoroscopic image sequence.

Figure 5:
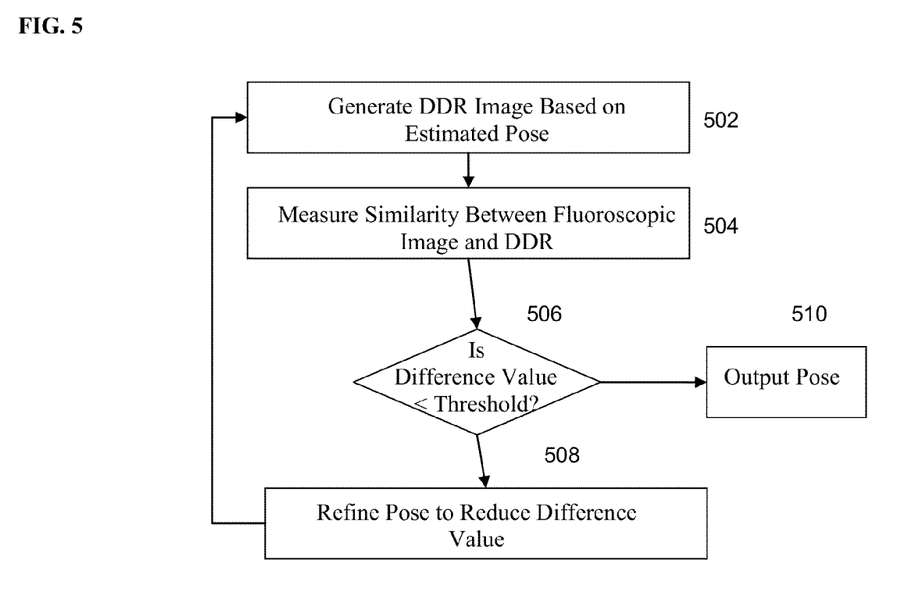
FIG. 5 illustrates a method of refining an estimated pose of an ultrasound probe according to an embodiment of the present invention.

At step 404, the estimated initial pose of the probe is refined. In particular, 2D/3D registration can be used to iteratively refine the pose estimation. FIG. 5 illustrates a method of refining an estimated pose of an ultrasound probe according to an embodiment of the present invention. The method of FIG. 5 can be used to implement step 404 of FIG. 4.

Figure 6:
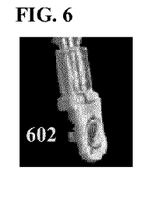
FIG. 6 illustrates a probe in 3D.

At step 502, a DRR image is generated based on the estimated pose of the probe. A 3D model of the probe is generated offline using DynaCT/CT. This model is aligned to the initialized position of the probe in 3D and used to generate a DRR. The DRR produces a representation of the probe which is visually similar to the image captured by the fluoroscopic. This enables a comparison between the two the DRR and the fluoroscopic image. At step 504, similarity between the fluoroscopic image and DRR is measured. The similarity may be measured using a difference value that represents an amount of difference between the fluoroscopic image and the DRR. That is, a small difference value indicates that the fluoroscopic image and the DRR are similar. At step 506, it is determined if the difference value between the fluoroscopic image and the DRR is below of given threshold. If the difference value is not below the threshold at step 506, the method proceeds to step 508. At step 508, the pose is refined based on the measured similarity. The pose can be refined by using a local search to determine a new pose that reduces the difference value measured between the fluoroscopic image and the DRR. After the pose is refined, the method returns to step 502 and a new DRR is generated based on the refined pose. The similarity is then measured between the new DRR and the fluoroscopic image at step 504 and the above described steps are repeated until the difference value is below the threshold. If the difference value is below the threshold at step 506, the method proceeds to step 510. At step 510, the pose of the probe is output and the method ends. FIG. 6 illustrates a probe 602 in 3D. The pose of the probe 602 was determined based on the probe detection results in the fluoroscopic image shown in FIG. 3.

Figure 7:
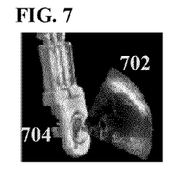
FIG. 7 illustrates a TEE image mapped to a 3D local coordinate system of a fluoroscopic image acquisition device.

Returning to FIG. 1, at step 110, the TEE image is mapped to the 3D coordinate system of fluoroscopic image acquisition device (e.g., C-arm device) based on the estimated pose of the probe in the 3D coordinate system. In particular, the TEE is mapped to the 3D coordinate system based on the estimated pose of the probe using Ultrasound calibration parameters. The ultrasound device (i.e., the TEE transducer is calibrated offline prior to the cardiac procedure, resulting in ultrasound calibration parameters. The ultrasound calibration parameters are used to estimate a transform that relates the coordinate system of the TEE image to the local coordinate system of the head of the TEE ultrasound probe. Since the pose of the probe is estimated in the 3D coordinate system of the fluoroscopic image acquisition device, the transform maps the TEE image to the 3D coordinate system of the fluoroscopic image acquisition device based on the relationship between the head of the TEE ultrasound probe and the TEE image. The calculation of the transform from the ultrasound calibration parameters may be performed using the method described in Gao et al., "Rapid Image Registration of Three-Dimensional Transesophageal Echocardiography and X-ray Fluoroscopy for the Guidance of Cardiac Interventions", In *Proceedings of the First International Conference on Information Processing in Computer-Assisted Interventions*, 2010, pages 124-134, which is incorporated herein by reference. FIG. 7 illustrates a TEE image 702 mapped to the 3D local coordinate system of a fluoroscopic image acquisition device based on the pose of the ultrasound probe 704.

Figure 8:
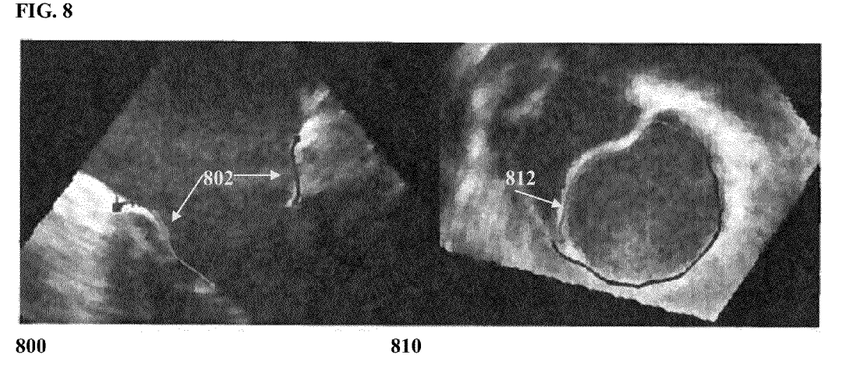
FIG. 8 illustrates exemplary mitral valve contours detected from X-Plane TEE images.

Returning to FIG. 1, at step 112, contours of an anatomical object are detected in the TEE image. For example, the contours of the mitral valve or the aortic valve can be detected in the TEE image. In an advantageous embodiment, the contours can be detected short and/or long axis TEE/X-Plane TEE images. The contours can be extracted using learning based detectors in a marginal space learning (MSL) framework. In an MSL framework, the idea is to detect an object (e.g., a 2D contour) in a series of parameter spaces having increasing dimensionality, instead of detecting the object directly in a full parameter space. In order to detect the contours of the mitral valve or the aortic valve in a TEE image, 2D rigid motion parameters can be detected using a first trained detector, followed by detection of the valve contours using a second trained detector based on the detected rigid motion contours. The detectors can be successively trained based on a database of annotated training data using a probabilistic boosting tree classifier with Haar features. In an advantageous implementation in which the received TEE image is a 3D TEE, random cuts of the 3D TEE are selected to generate the 2D X-plane TEE images, and then the contours of the mitral valve or the aortic valve detected are detected in the 2D X-plane TEE images generated by the random cuts of the 3D TEE. FIG. 8 illustrates exemplary mitral valve contours detected from X-Plane TEE images. The X-Plane TEE images include a long axis TEE image 800 and a short axis TEE image 810. As shown in FIG. 8, image 800 shows detected mitral valve contours 802 on the long axis image and image 810 shows a detected mitral valve contour 812 on the short axis image.

Returning to FIG. 1, at step 114, a patient-specific anatomical model extracted from a pre-operative CT image is aligned to the TEE image based on the contours detected in the TEE image. The pre-operative CT image is one or more 3D CT volume of the patient acquired prior to the fluoroscopic image and the TEE image are received. In an advantageous embodiment, the patient-specific anatomical model is a physiological model of the patient's cardiac structures. The physiological heart model can include mesh models for the four heart chambers (left ventricle, right ventricle, left atrium, and right atrium), four heart valves (aortic, mitral, pulmonary, and tricuspid), and the aorta. The patient-specific parameters of the physiological model can be estimated from using hierarchical approaches within an MSL framework. Detectors are successively trained based on annotated training data using Probabilistic Boosting Trees (PBT) with Haar and Steerable features, and consequently applied to estimate rigid motion parameters, followed by anatomical landmarks and surface structures. U.S. Pat. No. 7,916,919, issued Mar. 29, 2011, and entitled "System and Method for Segmenting Chambers of a Heart in a Three Dimensional Image", U.S. Pat. No. 8,009,887, issued Aug. 30, 2011, and entitled "Method and System for Automatic Quantification of Aortic Valve Function from 4D Computed Tomography Data Using a Physiological Model", and U.S. Publication No. 2012/0022843, entitled "Method and System for Comprehensive Patient-Specific Modeling of the Heart", the disclosures of which are incorporated herein by reference.

Figure 9:
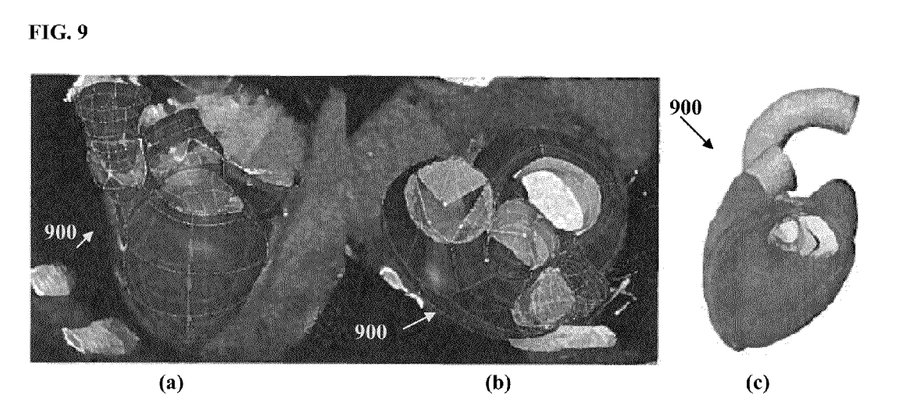
FIG. 9 illustrates an exemplary patient-specific physiological heart model extracted from a CT volume.

FIG. 9 illustrates an exemplary patient-specific physiological heart model extracted from a CT volume. Images (a) and (b) show the patient-specific physiological heart model 900 in two views of the CT volume and image (c) shows a 3D rendering of the patient-specific physiological heart model 900. As shown in FIG. 9, the patient-specific physiological heart model 900 includes a left ventricle, left atrium, right ventricle, right atrium, aortic valve, mitral valve, pulmonary valve, tricuspid valve, and ascending aorta.

Figure 10:
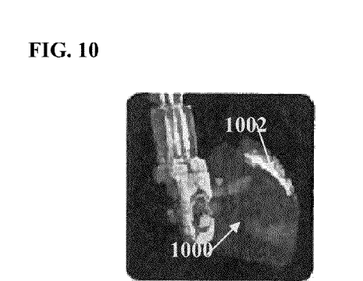
FIG. 10 illustrates a patient-specific physiological heart model mapped to a TEE ultrasound image.

The patient-specific physiological model extracted from the CT image is aligned to the TEE image by calculating a rigid transformation to map the detected contours in the TEE image to the corresponding anatomical structure in the patient-specific physiological model extracted from the pre-operative CT image. Shape features are extracted from the contours detected in the TEE image and used to match the contours with corresponding anatomy in the patient-specific physiological model. For example, the shape features described in L. Shapira et al., "Contextual Part Analogies in 3D Objects", *International Journal of Computer Vision* (2010) 89: 309-326, which is incorporated herein by reference, can be used to match the contours to the patient-specific physiological model, but the present invention is not limited thereto. A rigid transformation is then calculated to register the detected contours (e.g., mitral valve or aortic valve contours) in the TEE image with the corresponding anatomy (e.g., corresponding portions of the mitral valve model or the aortic valve model) in the patient-specific physiological heart model extracted from the pre-operative CT image. This rigid transformation provides a mapping between the pre-operative CT image and the TEE image. FIG. 10 illustrates a patient-specific physiological heart model 1002 mapped to a TEE ultrasound image 1000.

Figure 11:
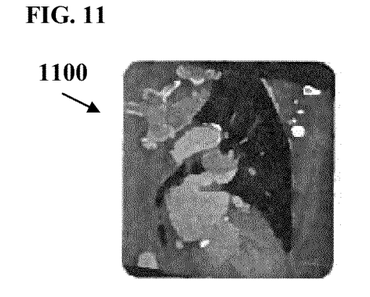
FIG. 11 illustrates an output image resulting from projecting a pre-operative CT image into a fluoroscopic image.

Returning to FIG. 1, at step 116, a final mapping between the pre-operative CT and the fluoroscopic image is determined. In particular, the final mapping is determined based on the mapping between the TEE image and pre-operative CT image and the mapping of the TEE image to the 3D coordinate system of the fluoroscopic image acquisition device. The final mapping maps the CT image or the patient-specific physiological model to the TEE image based on the transformation between the contours in the TEE image and the corresponding anatomy in the patient-specific physiological model in the CT image, and then maps the CT image or the patient-specific physiological model to fluoroscopic image coordinate system based on the mapping of the TEE image to the 3D coordinate system of the fluoroscopic image acquisition device. Accordingly, the final mapping can be used to map any point from the coordinate system of the pre-operative CT image to the coordinate system of the fluoroscopic image acquisition device. T At step 118, the pre-operative CT image is projected into the fluoroscopic image. The pre-operative CT image is projected into the fluoroscopic image using the final mapping in order to visualize the pre-operative CT image in the intra-operative fluoroscopy. In particular, since the final mapping maps the pre-operative CT image into the coordinate system of the fluoroscopic image acquisition device (e.g., C-arm device), the pre-operative image can be projected into the fluoroscopic image using a projection matrix associated with the fluoroscopic image. The resulting image can be displayed, for example, on a display of a computer system. FIG. 11 illustrates an output image 1100 resulting from projecting a pre-operative CT image into a fluoroscopic image.

Figure 12:
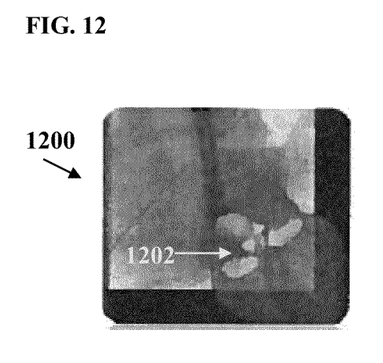
FIG. 12 illustrates a patient-specific model projected into a fluoroscopic image.

Returning to FIG. 1, at step 120, the patient-specific physiological model extracted from the pre-operative CT image is projected into the fluoroscopic image. The patient-specific physiological model is projected into the fluoroscopic image using the final mapping, thus visualizing the patient-specific model in the intra-operative fluoroscopy. In particular, since the final mapping maps the patient-specific physiological model from the image space of the pre-operative CT image into the coordinate system of the fluoroscopic image acquisition device (e.g., C-arm device), the patient-specific physiological model can be projected into the fluoroscopic image using a projection matrix associated with the fluoroscopic image. The resulting image can be displayed, for example, on a display of a computer system. FIG. 12 illustrates a patient-specific model 1202 projected into a fluoroscopic image 1200.

As described above, the model-based image fusion results can be visualized by projecting the pre-operative CT image into the fluoroscopic image (step 118) or by projecting the patient-specific physiological model into the fluoroscopic image (step 120), using the TEE image as an intermediate modality. The method of FIG. 1 may be repeated for each frame in a sequence of fluoroscopic images. In this case, the method of FIG. 1 can provide real time fusion of pre-operative CT data with frames of the fluoroscopic image sequence during a cardiac intervention procedure. Since each repetition of the method of FIG. 1 received a new frame of the fluoroscopic image sequence and a new TEE image, each frame of the fluoroscopic image sequence is calibrated with a current location of the TEE ultrasound probe. Accordingly, since the patient-specific model is aligned with each TEE image in order to determine the final mapping to the coordinate system of the fluoroscopic image acquisition device, the CT image or patient-specific model visualized in each frame of the fluoroscopic image sequence is motion compensated.

The method of FIG. 1, as described above, fuses pre-operative CT image data with intra-operative fluoroscopic images using TEE ultrasound images as an intermediate modality. However, the present invention is not necessarily limited to those imaging modalities. For example, other imaging modalities, such as magnetic resonance imaging (MRI), can used to generate the pre-operative image and patient-specific physiological model, and other types of ultrasound, such as Intracardiac Ultrasound (ICE), may be used in place of TEE.

Figure 13:
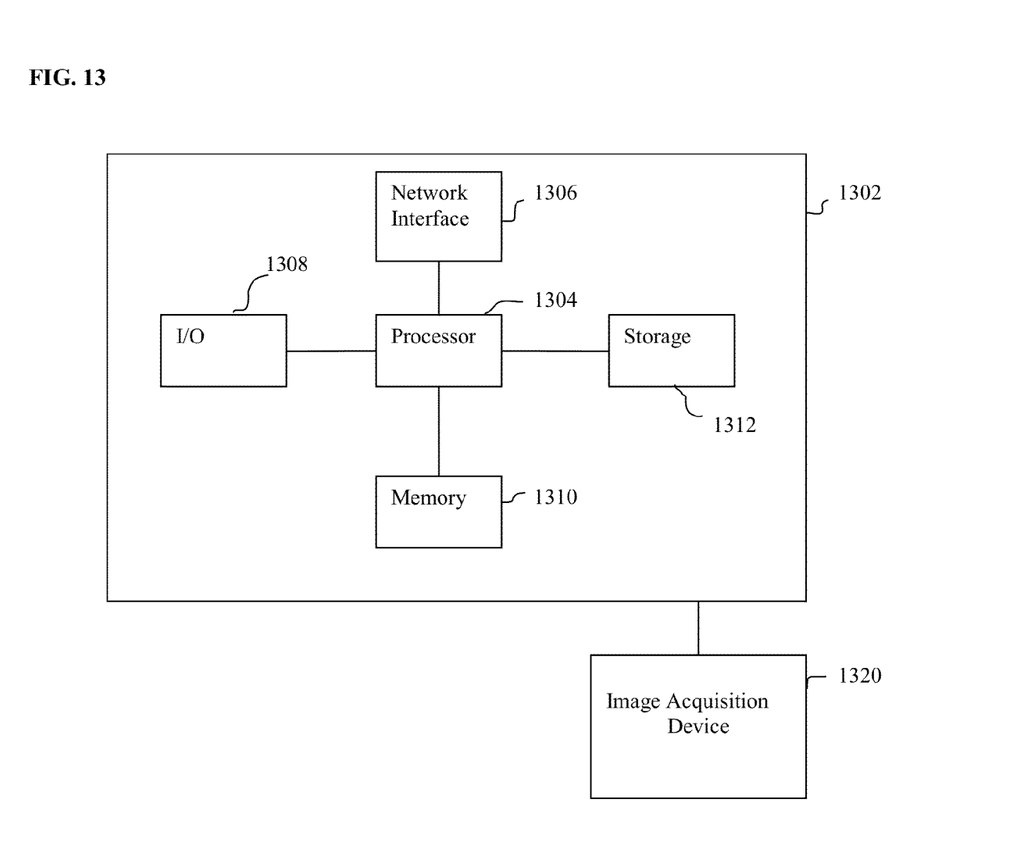
FIG. 13 is a high-level block diagram of a computer capable of implementing the present invention.

The above-described methods for model-based fusion of pre-operative image data and intra-operative fluoroscopic images using ultrasound images may be implemented on a computer using well-known computer processors, memory units, storage devices, computer software, and other components. A high-level block diagram of such a computer is illustrated in FIG. 13. Computer 1302 contains a processor 1304, which controls the overall operation of the computer 1302 by executing computer program instructions which define such operation. The computer program instructions may be stored in a storage device 1312 (e.g., magnetic disk) and loaded into memory 1310 when execution of the computer program instructions is desired. Thus, the steps of the methods of FIGS. 1, 4, and 5 may be defined by the computer program instructions stored in the memory 1310 and/or storage 1312 and controlled by the processor 1304 executing the computer program instructions. An image acquisition device 1320, such as a C-arm image acquisition device, can be connected to the computer 1302 to input image data to the computer 1302. It is possible to implement the image acquisition device 1320 and the computer 1302 as one device. It is also possible that the image acquisition device 1320 and the computer 1302 communicate wirelessly through a network. The computer 1302 also includes one or more network interfaces 1306 for communicating with other devices via a network. The computer 1302 also includes other input/output devices 1308 that enable user interaction with the computer 1302 (e.g., display, keyboard, mouse, speakers, buttons, etc.). One skilled in the art will recognize that an implementation of an actual computer could contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for fusing pre-operative computed tomography (CT) image data with a fluoroscopic image acquired using a fluoroscopic image acquisition device based on an ultrasound image acquired using an ultrasound probe, comprising:
   detecting a 2D location of the ultrasound probe in the fluoroscopic image;
   estimating a 3D pose of the ultrasound probe based on the detected 2D location of the ultrasound probe in the fluoroscopic image; and
   mapping the ultrasound image to a 3D coordinate system of the fluoroscopic image acquisition device based on the estimated 3D pose of the ultrasound probe;
   detecting contours of an anatomical structure in the ultrasound image;
   calculating a transformation between the ultrasound image and a pre-operative CT image based on the contours detected in the ultrasound image and a patient-specific physiological model extracted from the pre-operative CT image; and
   determining a final mapping between the pre-operative CT image and the fluoroscopic image based on the transformation between the ultrasound image and the patient-specific physiological model extracted from the pre-operative CT image and the mapping of the ultrasound image to the 3D coordinate system of the fluoroscopic image acquisition device.

2. The method of claim 1, further comprising:
   mapping the pre-operative CT image to the 3D coordinate system of the fluoroscopic image acquisition device using the final mapping; and
   projecting the pre-operative CT image into the fluoroscopic image using a projection matrix associated with the fluoroscopic image.

3. The method of claim 1, further comprising:
   mapping the patient-specific physiological model to the 3D coordinate system of the fluoroscopic image acquisition device using the final mapping; and
   projecting the patient-specific physiological model into the fluoroscopic image using a projection matrix associated with the fluoroscopic image.

4. The method of claim 1, wherein the step of detecting a 2D location of the ultrasound probe in the fluoroscopic image comprises:
   detecting the 2D location of the ultrasound probe using a probe detector trained based on training data using a learning based method.

5. The method of claim 1, wherein the step of estimating a 3D pose of the ultrasound probe based on the detected 2D location of the ultrasound probe in the fluoroscopic image comprises:
   estimating an initial 3D pose of the ultrasound probe based on the detected 2D location of the ultrasound probe in the fluoroscopic image; and
   refining the initial 3D pose using iterative 2D-3D registration.

6. The method of claim 5, wherein the step of estimating an initial 3D pose of the ultrasound probe based on the detected 2D location of the ultrasound probe in the fluoroscopic image comprises:
   estimating a 3D position and orientation of the ultrasound probe based on the detected 2D location of the ultrasound probe using a series of trained learning based classifiers.

7. The method of claim 5, wherein the step of refining the initial 3D pose using iterative 2D-3D registration comprises:
   (a) aligning a 3D model of the ultrasound probe to current estimated 3D pose;
   (b) generating a digital reconstructed radiograph (DRR) from the aligned 3D model of the ultrasound probe;
   (c) measuring a difference value between the fluoroscopic image and the DRR; and
   (d) refining the current estimated 3D pose to reduce the difference value between the fluoroscopic image and the DRR.

8. The method of claim 7, wherein the step of refining the initial 3D pose using iterative 2D-3D registration further comprises:
   (e) repeating steps (a)-(d) until the difference value between the fluoroscopic image and the DRR is less than a threshold.

9. The method of claim 4, wherein the step of mapping the ultrasound image to a 3D coordinate system of the fluoroscopic image acquisition device based on the estimated 3D pose of the ultrasound probe comprises:
   calculating a transformation to map the ultrasound image to the 3D coordinate system of the fluoroscopic image acquisition device based on an estimated position and orientation of the ultrasound probe using ultrasound configuration parameters.

10. The method of claim 1, wherein the step of detecting contours of an anatomical structure in the ultrasound image comprises:
    detecting contours of at least one of a mitral valve and an aortic valve in the ultrasound image.

11. The method of claim 1, wherein the step of detecting contours of an anatomical structure in the ultrasound image comprises:
    detecting the contours in the ultrasound image using a series of trained classifiers.

12. The method of claim 11, wherein the step of detecting the contours in the ultrasound image using a series of trained classifiers comprises:
    detecting 2D rigid motion parameters in the ultrasound image using a first trained classifier; and
    detecting the contours in the ultrasound image based on the detected 2D rigid motion parameters using a second trained classifier.

13. The method of claim 1, wherein the ultrasound image is a 3D ultrasound image and the step of detecting contours of an anatomical structure in the ultrasound image comprises:
    generating a plurality of 2D ultrasound images by randomly cutting the 3D ultrasound image; and
    detecting the contours in the plurality of 2D ultrasound images.

14. The method of claim 1, wherein the step of calculating a transformation between the ultrasound image and a pre-operative CT image based on the contours detected in the ultrasound image and a patient-specific physiological model extracted from the pre-operative CT image comprises:
    matching the contours detected in the ultrasound image with corresponding portions of the patient-specific physiological model using shape features extracted from the detected contours; and
    calculating a transformation to register the contours detected in the ultrasound image with the corresponding portions of the patient-specific physiological model.

15. The method of claim 1, wherein the ultrasound image is a transesophageal echocardiography (TEE) image and the ultrasound probe is a TEE ultrasound probe used to acquire the TEE image.

16. The method of claim 1, wherein the patient-specific physiological model comprises a patient-specific physiological heart model.

17. An apparatus for fusing pre-operative computed tomography (CT) image data with a fluoroscopic image acquired using a fluoroscopic image acquisition device based on an ultrasound image acquired using an ultrasound probe, comprising:
    means for detecting a 2D location of the ultrasound probe in the fluoroscopic image;
    means for estimating a 3D pose of the ultrasound probe based on the detected 2D location of the ultrasound probe in the fluoroscopic image; and
    means for mapping the ultrasound image to a 3D coordinate system of the fluoroscopic image acquisition device based on the estimated 3D pose of the ultrasound probe;
    means for detecting contours of an anatomical structure in the ultrasound image;
    means for calculating a transformation between the ultrasound image and a pre-operative CT image based on the contours detected in the ultrasound image and a patient-specific physiological model extracted from the pre-operative CT image; and
    means for determining a final mapping between the pre-operative CT image and the fluoroscopic image based on the transformation between the ultrasound image and the patient-specific physiological model extracted from the pre-operative CT image and the mapping of the ultrasound image to the 3D coordinate system of the fluoroscopic image acquisition device.

18. The apparatus of claim 17, further comprising:
    means for projecting the pre-operative CT image into the fluoroscopic image based on the final mapping.

19. The apparatus of claim 17, further comprising:
    means for projecting the patient-specific physiological model into the fluoroscopic image based on the final mapping.

20. The apparatus of claim 17, wherein the means for detecting contours of an anatomical structure in the ultrasound image comprises:
    means for detecting contours of at least one of a mitral valve and an aortic valve in the ultrasound image.

21. The apparatus of claim 17, wherein the ultrasound image is a 3D ultrasound image and the means for detecting contours of an anatomical structure in the ultrasound image comprises:
    means for generating a plurality of 2D ultrasound images from the 3D ultrasound image; and
    means for detecting the contours in the plurality of 2D ultrasound images.

22. The apparatus of claim 17, wherein the means for calculating a transformation between the ultrasound image and a pre-operative CT image based on the contours detected in the ultrasound image and a patient-specific physiological model extracted from the pre-operative CT image comprises:
    means for matching the contours detected in the ultrasound image with corresponding portions of the patient-specific physiological model; and
    means for calculating a transformation to register the contours detected in the ultrasound image with the corresponding portions of the patient-specific physiological model.

23. A non-transitory computer readable medium storing computer program instructions for fusing pre-operative computed tomography (CT) image data with a fluoroscopic image acquired using a fluoroscopic image acquisition device based on an ultrasound image acquired using an ultrasound probe, the computer program instructions when executed on a processor cause the processor to perform operations comprising:
    detecting a 2D location of the ultrasound probe in the fluoroscopic image;
    estimating a 3D pose of the ultrasound probe based on the detected 2D location of the ultrasound probe in the fluoroscopic image; and
    mapping the ultrasound image to a 3D coordinate system of the fluoroscopic image acquisition device based on the estimated 3D pose of the ultrasound probe;
    detecting contours of an anatomical structure in the ultrasound image;
    calculating a transformation between the ultrasound image and a pre-operative CT image based on the contours detected in the ultrasound image and a patient-specific physiological model extracted from the pre-operative CT image; and
    determining a final mapping between the pre-operative CT image and the fluoroscopic image based on the transformation between the ultrasound image and the patient-specific physiological model extracted from the pre-operative CT image and the mapping of the ultrasound image to the 3D coordinate system of the fluoroscopic image acquisition device.

24. The non-transitory computer readable medium of claim 23, wherein the operations further comprise:
    mapping the pre-operative CT image to the 3D coordinate system of the fluoroscopic image acquisition device using the final mapping; and projecting the pre-operative CT image into the fluoroscopic image using a projection matrix associated with the fluoroscopic image.

25. The non-transitory computer readable medium of claim 23, wherein the operations further comprise:
   mapping the patient-specific physiological model to the 3D coordinate system of the fluoroscopic image acquisition device using the final mapping; and
   projecting the patient-specific physiological model into the fluoroscopic image using a projection matrix associated with the fluoroscopic image.

26. The non-transitory computer readable medium of claim 23, wherein the operation of detecting contours of an anatomical structure in the ultrasound image comprises:
   detecting contours of at least one of a mitral valve and an aortic valve in the ultrasound image.

27. The non-transitory computer readable medium of claim 23, wherein the operation of detecting contours of an anatomical structure in the ultrasound image comprises:
   detecting the contours in the ultrasound image using a series of trained classifiers.

28. The non-transitory computer readable medium of claim 23, wherein the ultrasound image is a 3D ultrasound image and the operation of detecting contours of an anatomical structure in the ultrasound image comprises:
   generating a plurality of 2D ultrasound images by randomly cutting the 3D ultrasound image; and
   detecting the contours in the plurality of 2D ultrasound images.

29. The non-transitory computer readable medium of claim 23, wherein the operation of calculating a transformation between the ultrasound image and a pre-operative CT image based on the contours detected in the ultrasound image and a patient-specific physiological model extracted from the pre-operative CT image comprises:
   matching the contours detected in the ultrasound image with corresponding portions of the patient-specific physiological model using shape features extracted from the detected contours; and
   calculating a transformation to register the contours detected in the ultrasound image with the corresponding portions of the patient-specific physiological model.

\* \* \* \* \*